United States Patent [19]
Gentelia et al.

[11] Patent Number: 5,468,240
[45] Date of Patent: Nov. 21, 1995

[54] MANUAL CONTROL DEVICE FOR LAPAROSCOPIC INSTRUMENT

[75] Inventors: John S. Gentelia, Madison; Ronald E. Eggan, Jr., Rome; Frank R. Williams; William Wheatley, both of Utica, all of N.Y.

[73] Assignee: Conmed Corporation, Utica, N.Y.

[21] Appl. No.: 985,147

[22] Filed: Dec. 3, 1992

[51] Int. Cl.⁶ ................................................. A61B 17/39
[52] U.S. Cl. ................... 606/42; 606/45; 606/49; 604/34; 604/35
[58] Field of Search ....................... 606/41, 42, 45, 606/48, 49, 50; 604/34, 35, 902

[56] References Cited

U.S. PATENT DOCUMENTS

| | | |
|---|---|---|
| 4,617,013 | 10/1986 | Betz . |
| 4,696,669 | 9/1987 | Menhusen . |
| 4,872,454 | 10/1989 | DeOliveira et al. . |
| 5,000,754 | 3/1991 | DeOliveira et al. . |
| 5,035,695 | 7/1991 | Weber, Jr. et al. . |
| 5,071,418 | 12/1991 | Rosenbaum . |
| 5,088,997 | 2/1992 | Delahuerga et al. . |
| 5,098,430 | 3/1992 | Fleenor . |
| 5,195,959 | 3/1993 | Smith ................................ 606/42 X |
| 5,254,083 | 10/1993 | Gentelia et al. ..................... 604/35 |
| 5,254,117 | 10/1993 | Rigby et al. ........................ 606/42 |
| 5,295,956 | 3/1994 | Bales et al. ...................... 606/49 X |

*Primary Examiner*—Lee S. Cohen
*Attorney, Agent, or Firm*—Larson & Taylor

[57] ABSTRACT

A manual control device for laparoscopic patient treatment by use of electrical curetage or coagulation, with means for clearing the surgical sight by irrigation or suction, finger operated buttons controlling the various functions, and an interlock mechanism disabling the electrical functions when a push button is depressed to enable irrigation or suction.

5 Claims, 2 Drawing Sheets

5,468,240

MANUAL CONTROL DEVICE FOR LAPAROSCOPIC INSTRUMENT

FIELD OF THE INVENTION

The present invention relates to surgical medical apparatus, and more particularly to a manual control device for laparoscopic devices utilizing electrical treatment such as curetage and coagulation, as well as means for clearing the surgical site as by vacuum and fluid pressure.

BACKGROUND OF THE INVENTION

Electrical curetage and coagulation are well known in the art, as are instruments for applying vacuum and fluid pressure at the surgical site. It is known to utilize flexible tubes for suction and irrigation, together with valves for opening and closing the tubes. The use of such tubes and closing of flexible tubes by pinching or the like is disclosed, for example, in the commonly owned, application of Gentilia et al, Ser. No. 07/833,000, filed Feb. 10, 1992, now U.S. Pat. No. 5,254,083.

The prior art devices utilize foot pedals as well as digitally operated push buttons for controlling the various functions. However those devices do not provide the secure operation provided by the ingenious structure of the present invention, in assuring that neither suction nor irrigation can be applied to the surgical site at the same time as electrical curetage or coagulation is being carried out. Exemplary patents of interest are: U.S. Pat. Nos. 4,617,013; 4,696,669; 4,872,454; 5,000,754; 5,035,695; 5,071,418; 5,098,997; and U.S. Pat. No. 5,098,430.

SUMMARY OF THE INVENTION

The present invention provide a novel manual control device for a laparoscopic electrical patient treatment instrument, comprising handle means having a plurality of digitally (finger) operable control means such as push buttons, and electrical circuit means for controlling electrical treatment at the surgical site, such as curetage and coagulation. Conduit means provide for applying suction or irrigation at the surgical site. The control means operate switch means in the circuit and control flow through the conduit means. Interlock means disables the electrical circuit when the control means enable flow through the conduit means.

The importance of securing against application of suction or irrigation to the surgical site concurrently with curetage or coagulation operation, cannot be overemphasized. These electrical treatments involve application of high voltage, high frequency waveforms at the surgical site. In the coagulating mode, the current is generally delivered in short pulses, with pauses between pulses. In the cutting or curetage mode, the voltage is applied continuously to generate high heat. The surgeon applying such treatment must be able to change quickly and accurately between electrical treatment and application of suction or irrigation. Yet if electrical treatment is carried out while either suction or irrigation is being applied, the electrical treatment can be adversely affected. For example, the temperature at the surgical site could be drastically lowered by suction or fluid, or irrigation fluid could be rapidly expanded or vaporized in an explosive manner.

Thus it is extremely important, and it is an object of the present invention, to provide a control device which assures that the electrical circuit for curetage and coagulation operation is disabled when either suction or irrigation are being applied.

Other objects and many of the attendant advantages of the present invention will become apparent upon consideration of the following detailed description of a preferred form of the invention, taken in connection with the accompanying drawing, in which:

DESCRIPTION OF THE PREFERRED EMBODIMENT

Figure 1:
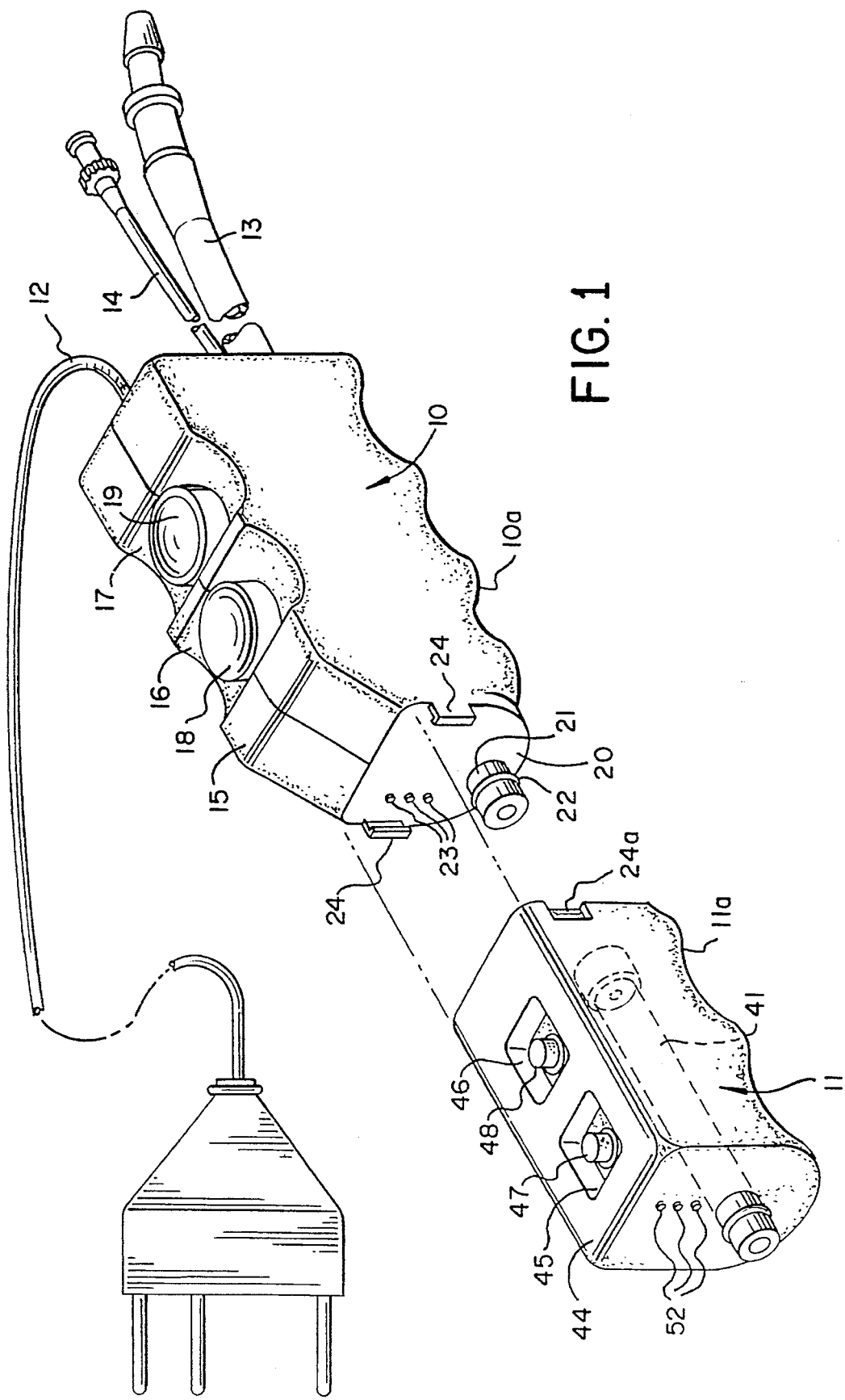
FIG. 1 is a perspective view of the control device, with the two modules separated.

Referring now more specifically to the drawing, wherein like numerals indicate like parts throughout the several views, there is shown in FIG. 1 a handle formed of two parts 10 and 11 of molded, electrically insulating plastic material. Part 10 is the module for controlling suction and irrigation; part 11 is the module for controlling electrical curetage and coagulation. In use, the two modules are joined together. Connected to the rear of module 10 are a three wire electrical connector 12 and two flexible tubes 13 and 14, the two tubes being provided for connection, respectively, to a source of vacuum and a source of fluid pressure. The bottom surface of both modules is contoured to provide a convenient hand grip as at 10a and 11a.

Figure 2:
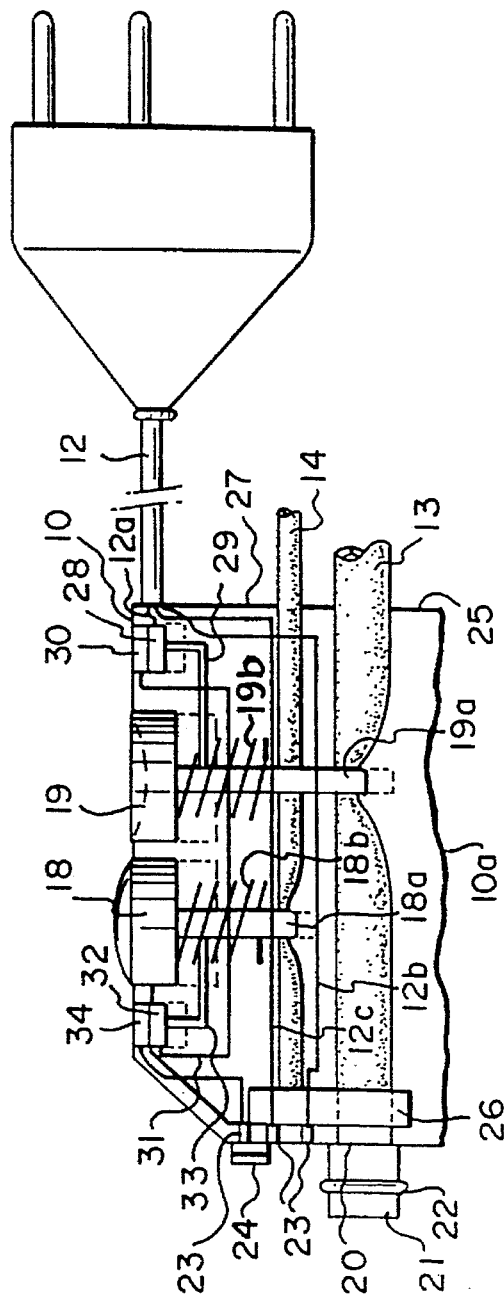
FIG. 2 is a diagrammatic side view of teh fluid control module showing its interior, depressed positions of push buttons and related parts being indicated in dotted lines.

The upper surfaces 15 of module 10 has two spaced indentations 16, 17, with a push button 18 in indentation 16 and a push button 19 in indentation 17. As seen in FIG. 2, push button 19 has a concave upper surface to provide ready touch indentation of that button, and may be of a different color from button 18, which may have a convex surface.

Projecting from the front wall 20 of module 10 is common fluid tube portion 21 which carries an "O" ring gasket. Three electrical contacts 23 are located on the front wall 20, as are two positioning projections 24 which extend forwardly from front surface 20.

Continuing with the description of module 10, and referring to FIG. 2, the outer wall of module 10 is indicated at 25 and the rear wall at 27. Flexible tubes 13 and 14 extend through wall 27 into the interior of the module and extend toward front wall 20. They connect to a small chamber, the walls of which are indicated at 26, from which a single, stiffer tube emerges to form tube 21 extending from front wall 20.

Figure 4:
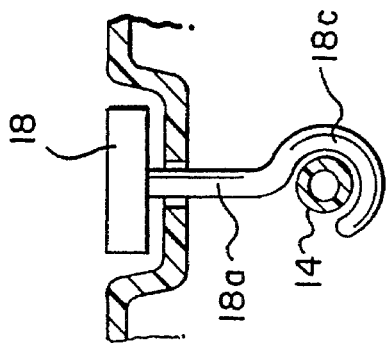
FIG. 4 is a detail view of one of the push button controls with its associated conduit in open condition.

Push buttons 18 and 19 are attached, respectively, to downwardly extending arms 18a and 19a and are urged by springs 18b and 19b to their uppermost positions in which they are shown in FIG. 2. The springs are fixed at their lower ends to the module housing by means not shown. Arms 18a and 19a have a hook shaped configuration at the their lower ends to receive the respective tubes 13 and 14 as shown at 18c for arm 18a in FIG. 4. As shown in FIG. 4, pushbutton 18 is in its depressed position, so that tube 14, which provides conduit for irrigation fluid, is open and irrigation is enabled. This is the position shown in dotted lines in FIG. 2.

In their normal, upwardly biased positions as shown in solid lines in FIG. 2, the hook shaped portions at the lower ends of arms 18a and 19a pinch flexible tubes 14 and 15 to shut of any flow therethrough. To enable flow though either tube, the appropriate controlling push button 18 or 19 is depressed to the dotted line position of FIG. 2 against the spring bias.

FIG. 2 shows three wire electrical circuit connector 12 entering rear wall 27 of module 10. Common lead 12a thereof is connected to a switch contact 28 mounted on an extension 29 of arm 19a so that contact 28 moves up and down with arm 19a. In its upper position as shown in FIG. 2, contact 28 engages a fixed contact 30 mounted on the housing. Fixed contact 30 is connected by wire 31 to a switch contact 32 mounted on an extension 33 of arm 18a so as to be moveable up and down with push button 18 and arm 18a. Moveable contact 32 engages a fixed contact 34 mounted on the module housing when push button 18 is in its upper position. Contact 34 is connected to upper contact 23 on front wall 20.

The other two electrical leads 12a and 12c, one for curetage and one for coagulation, are connected to separate ones of the lower two contacts 23 on front wall 20 of the module.

Figure 3:
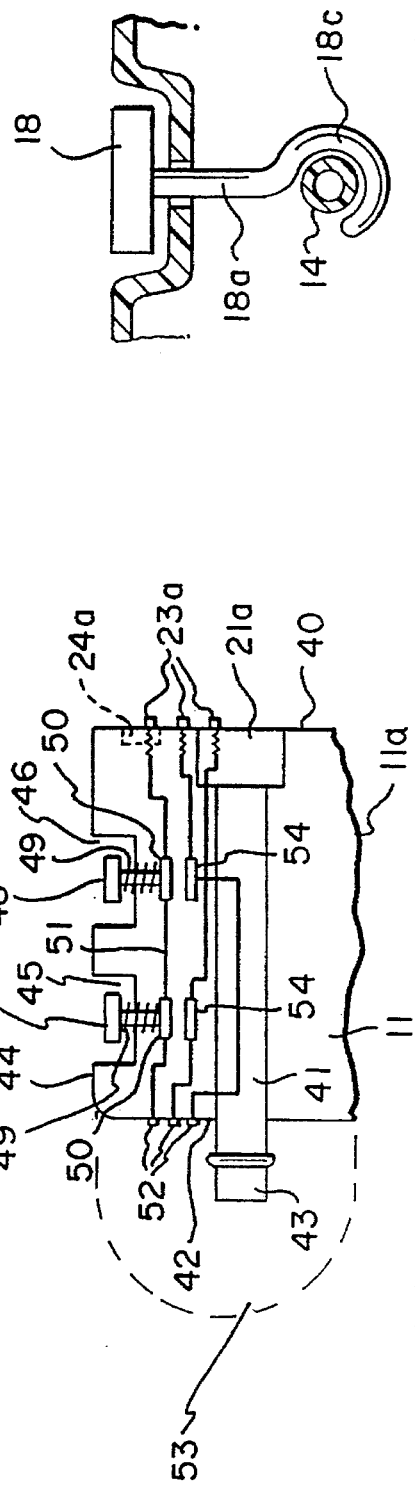
FIG. 3 is a view similar to FIG. 2, but showing the interior of the electrical control module.

Referring now to the showing of module 11 in FIG. 3, it has a rear wall 40 configured to match the front wall 20 of module 10. In each side wall there is a notch 24a to receive a positioning projection 24 when the modules are joined together. This mating assures proper positioning of the two modules. Also on rear wall 40 are three electrical contacts 23a to mate with contacts 23 on front wall 20 of module 10. The contacts may be spring pressed.

Opening 21a in rear wall 40 is provided for fluid tight reception of conduit tube 21 projecting from front wall 20 of module 10. Opening 21a is connected to a conduit tube 41 which extends out of the front wall 42 of module 11 at 43 to provide connection to a surgical instrument, not shown, but indicated by broken lines at 53. Extension 43 may be threaded or otherwise adapted, as by an "O" ring, for sealed connection to the surgical instrument (not shown).

Upper surface 44 of module 11 has two spaced indentations 45 and 46 in which are located push buttons 47 and 48 respectively. These buttons are different in shape and size from buttons 18, 19. Springs 49 bias these buttons to an upper position. The two push button are connected to respective switch contacts 50, so that depression of button 47 or 48 depressed one of the contacts 50. These contacts are connected in serial with the common line connected to upper contact 23a, as shown at 51. This line terminates at a contact 52 on front face 42 of module 11 which latter contact cooperates with the surgical instrument 53, details form no part of this invention.

Two fixed contacts 54 are positioned so that each one cooperates with one of the moveable contacts 50. One contact 54 is connected to one of the lower two contacts 23a and then to one of the lower two contacts 52. The other fixed contact 54 is connected to the other lower contact 23a and then to the remaining lower contact 52. It will be seen that when one of the buttons 47, 48 is depressed against the spring bias, its associated contact 50 will engage the adjacent fixed contact 54 to close the circuit to one of the two lower contacts 52. Thus control buttons 47, 48, control respectively, electrical curetage and coagulation.

OPERATION

In use, front surface 20 of module 10 is brought into contact with rear surface 40 of module 11, with projecting tube portion 21 seated in opening 21a and projections 24 seated in notches 24a. The appropriate surgical instrument indicated in dotted lines at 53 is attached to the front surface of module 11. The plug on the end of electrical connector is plugged into a suitable electrical supply and tubes 14 and 15 are connected, respectively, to a source of irrigation fluid and a vacuum source.

The surgeon then uses the control device by pressing the appropriate push button control to select curetage, coagulation, suction or irrigation, being confident that inadvertent depression of either button 18 or 19 will shut off electrical operation by disabling the common lead due to separating of contacts 228, 30 or 32, 34.

It will be understood that modifications and variations of the present invention are possible in light of the above teachings. For example, the handle could be made in one instead of two modules if it is not desired to have the manufacturing advantage of making it in two modules. Another variation would comprise compressing the flexible tubes against stops projecting from the inner surface of the housing of module 10 and located above the tubes.

We claim:

1. A manual control device for a laparoscopic electrical patient treatment instrument, said device comprising, a handle, conduit means extending through said handle for effecting connection to a vacuum source and a fluid pressure source, an electrical circuit extending through said handle, said handle comprising two mating parts, a first said part operatively associated with said electrical circuit and having a first digitally operable control means for controlling electrical curetage and electrical coagulation, a second said part having a second digitally operable control means for controlling vacuum and fluid pressure passing through said conduit means, and interlock means disabling said electrical circuit upon actuation of said second control means.

2. A control device as set forth in claim 1 wherein:

said electrical circuit comprises a three wire system with a common lead and separate leads for curetage and coagulation, respectively, said interlock means operable by interruption of said common lead.

3. A control device as set forth in claim 1, wherein:

at least portions of said conduit means being flexible, said second control means engaging said flexible portions of said conduit means to close said conduit means.

4. A control device as set forth in claim 1, wherein:

said second digitally operable control means have differently shaped contact surfaces to facilitate identification.

5. A control device as set forth in claim 1, wherein:

said first digitally operable control means are located in surface indentations in said handle as a safeguard against inadvertent operation.

\* \* \* \* \*